(12) United States Patent
Mouton

(10) Patent No.: US 6,653,520 B1
(45) Date of Patent: Nov. 25, 2003

(54) WOUND DRESSING

(75) Inventor: Johannes Petrus Mouton, Centurion (ZA)

(73) Assignee: Innovative Global Inc., Tortola (VG)

( * ) Notice: Subject to any disclaimer, the term of this patent is extended or adjusted under 35 U.S.C. 154(b) by 0 days.

(21) Appl. No.: 09/806,225

(22) PCT Filed: Sep. 23, 1999

(86) PCT No.: PCT/IB99/01570
§ 371 (c)(1),
(2), (4) Date: Jun. 22, 2001

(87) PCT Pub. No.: WO00/18343
PCT Pub. Date: Apr. 6, 2000

(51) Int. Cl.[7] .................................................. A61F 13/00
(52) U.S. Cl. .............................. 602/45; 602/41; 602/42
(58) Field of Search ....................... 602/41–59; 604/383

(56) References Cited
U.S. PATENT DOCUMENTS 4,307,152 A  * 12/1981 Mathes et al. .............. 428/373
5,632,731 A  *  5/1997 Patel .......................... 602/59

FOREIGN PATENT DOCUMENTS

| EP | 0 151 018 | 8/1985 |
| EP | 0 849 388 | 6/1998 |
| WO | 93/22486 | 11/1993 |
| WO | 96/36304 | 11/1996 |

* cited by examiner

Primary Examiner—Kim M. Lewis
(74) Attorney, Agent, or Firm—Foley & Lardner

(57) ABSTRACT

A wound dressing includes a first and a second absorbent layer, each absorbent layer being of a non-woven fabric of fibers, and each being able to absorb liquid and a screen comprising polyester and cotton fibers between, and bonded to, the two absorbent layers. The bonded absorbent layers and the screen form essentially a single, layered fabric body. The bonding between the first and second absorbent layers and the screen is brought about by a needle-punching process in which the punching density is 1700–1900 punches per square cm.

33 Claims, 1 Drawing Sheet

WOUND DRESSING

According to a first aspect of the invention, there is provided a wound dressing which includes
- a first and a second absorbent layer, each absorbent layer being of a non-woven fabric of fibres, and each being able to absorb liquid; and
- a screen comprising polyester and cotton fibres between, and bonded to, the two absorbent layers, so that the two absorbent layers and the screen form essentially a single, layered fabric body, the bonding between the first and second absorbent layers and the screen being brought about by a needle-punching process in which the punching density is about 1700–1900 punches per square cm.

By "punching density" is meant the number of times a needle perforates the absorbent layers and the screen per square cm in order to bond them together. This is typically conducted on a needleloom which has a needle board with about 30 000 needles and about 6 000 needles per linear meter, at a punching rate of about 300 punches per square cm.

Preferably, the bonding between the first and second absorbent layers may be brought about by a needle-punching process in which the punching density is about 1800 punches per square cm.

The fibres may be porous fibres.

The wound dressing may include at least one liquid permeable layer which is substantially non-adherent to human or animal tissue overlaying, and bonded to, at least one of the absorbent layers.

The wound dressing may include a further liquid permeable layer disposed such that the single, layered fabric body is sandwiched between the two liquid permeable layers.

Each absorbent layer may be of porous polyester fibres. The screen may comprise 80% polyester and 20% cotton fibres. It may have a thread density of about 120 to 150 threads per square inch. It may have a yarn count of about 32 to 40. It may have a weight per unit area of approximately 100 g/m².

The absorbent layers of non-woven fabric may be in the form of two fibre batts fabricated on a needleloom, each being made of 100% polyester fibre. The fibre batts may have a fineness of about 1.5 denier and a fibre length of about 7–8 cm, preferably about 7,62 cm (i.e. about 3 inches). They may have a weight per unit area of approximately 300 g/m².

The single, layered fabric body may have a mass of about 700–750 g/m². It may have a thickness of not more than about 3 mm.

The liquid permeable layer may be of a foraminous or perforated synthetic polymeric material. The synthetic polymeric material may be selected from "MYLAR" (trade name) and "TELFA" (trade name).

The bonding between the or each liquid permeable layer and the or each absorbent layer may be achieved by heat treatment under pressure.

According to another aspect of the invention there is provided a method of making a wound dressing, the method including the steps of
- fabricating two needle-punched fibre bans of fibres on a needleloom;
- fabricating a tightly woven screen of polyester and cotton fibres;
- locating the screen between the needle-punched fibre batts to form a composite structure in which the screen forms an inner layer between the two fibre batts; and
- needle-punching the composite structure on a needleloom to produce a single, layered fabric body in a needle-punching process in which the punching density is about 1700–1900 punches per square cm.

Preferably, the punching density will be about 1800 punches per square cm.

The method may include the further step of securing a liquid permeable layer, which is substantially non-adherent to human or animal tissue, to at least one side of the layered fabric body.

The needle-punched fibre batts may be of porous polyester. The screen may be fabricated of 80% polyester and 20% cotton yarns. It may be fabricated to have a thread density of about 120 to 150 threads per square inch. It may be fabricated to have a yarn count of about 32 to 40. It may be fabricated to have a weight per unit area of approximately 100 g/m².

The composite structure may be needle-punched to produce a single layered fabric body having a mass of about 700–750 g/m². The needle punching process may be repeated according to the thickness or effect desired. The composite structure may be needle-punched so that the thickness of the single layered fabric body will typically be not more than about 3 mm.

The fibre batts may have a fineness of about 1.5 denier. They may be fabricated to have a weight per unit area of approximately 300 g/m².

The liquid permeable layer may be of foraminous or perforated synthetic polymeric material. It may be selected from "MYLAR" (trade name) and "TELFA" (trade name).

Securing the liquid permeable layer to the at least one side of the layered fabric body may be achieved by heat treatment under pressure.

The invention extends to a method of removing exudate from a wound, the method including the step of applying to an exudating wound at least one wound dressing as hereinbefore described.

The invention will now be described, by way of example, with reference to the following drawings, in which.

Figure 1:
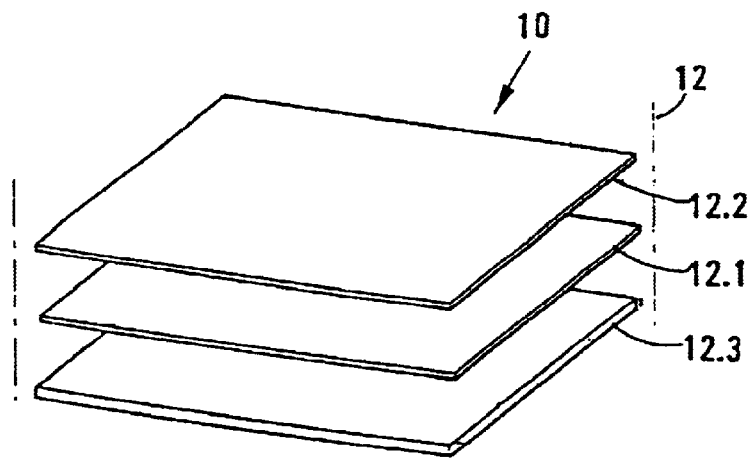
FIG. 1 is a schematic, exploded three-dimensional view of a wound dressing in accordance with the invention.

Referring to FIG. 1, reference numeral 10 generally indicates a wound dressing in accordance with the invention.

The wound dressing 10 is shown in exploded view in the drawing. The dressing 10 includes a first absorbent layer in the form of a fibre batt 12.2 and a second absorbent layer in the form of a fibre batt 12.3. The fibre batts 12.2 and 12.3 are made of non-woven fabric comprising porous polyester fibres. The dressing 10 includes a tightly woven screen 12.1 comprising polyester and cotton fibres sandwiched between the two fibre batts 12.2 and 12.3. The screen 12.1 is of a woven fabric comprising 80% polyester and 20% cotton yarns and has a thread density of about 120 to 150 threads per square inch, a yarn count of about 32 to 40 and a weight of about 100 g/m². The two absorbent layers 12.2 and 12.3 and the screen form essentially a single, layered fabric body, indicated in the drawing by reference numeral 12.

Figure 2:
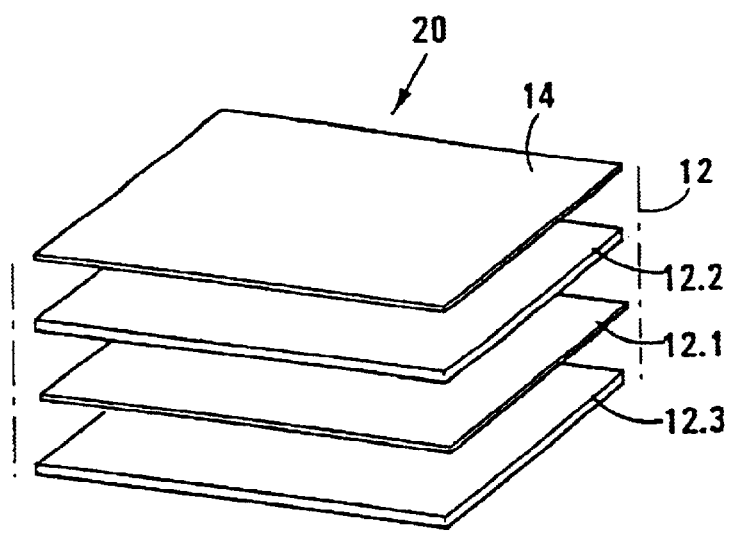
FIG. 2 is a schematic, exploded three-dimensional view of another embodiment of a wound dressing in accordance with the invention.

Referring to FIG. 2, reference numeral 20 generally indicates another embodiment of a wound dressing in accordance with the invention.

The wound dressing 20 resembles the wound dressing 10 and the same numbers have been used to indicate the same or similar features of the dressings 20 and 10. The dressing 20 differs from the dressing 10 only in that an outer liquid permeable layer 14 is secured to the fibre batt 12.2 so that the wound dressing 20 comprises four separate layers rather than three as in the wound dressing 10.

Figure 3:
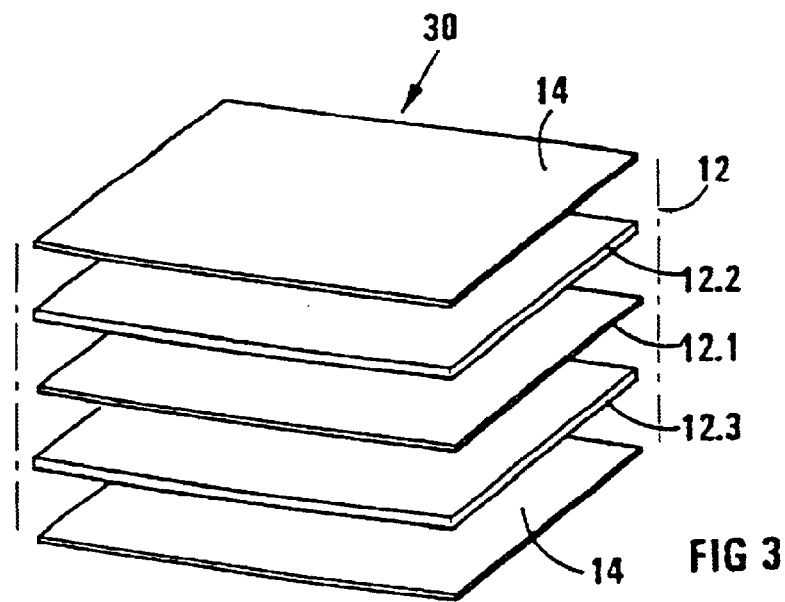
FIG. 3 is a schematic, exploded three-dimensional view of another embodiment of a wound dressing in accordance with the invention.

Referring to FIG. 3, reference numeral 30 generally indicates another embodiment of a wound dressing in accordance with the invention. The wound dressing 30 resembles the wound dressing 20 and the same numbers have been used to indicate the same or similar features of the dressings 30 and 20. The dressing 30 differs from the dressing 20 only in that a further outer liquid permeable layer 14 is secured to the fibre batt 12.3 so that the wound dressing 30 comprises five separate layers rather than four as in the wound dressing 20.

The liquid permeable layer 14 is bonded to the composite layer 12 by heat treatment under pressure. In a preferred embodiment of the invention the liquid permeable layers are of the material manufactured by Kendall (Pty) Limited and sold under the name "MYLAR" or the material manufactured by Macmed Healthcare Limited and sold under the trade name "TELFA".

The fibre batts 12.2 and 12.3 are fabricated on a needleloom. Each fibre batt 12.2, 12.3 is made of 100% polyester fibre, with a fineness of about 1.5 denier, a fibre length of about 7,62 cm (about 3 inches) and each has a weight of about 300 g/m$^2$. The two fibre batts 12.2 and 12.3 are needle-punched onto each side of the screen 12.1 thus making one completed fibre batt or single, layered fabric body with a middle screen 12.1 and which weighs about 700 g/cm$^2$. The thickness of the single, layered fabric body 12 is not more than about 3 mm.

The needle-punching process by which the fibre batts 12.2 and 12.3 and the screen 12.1 are bonded together is conducted on a needleloom which has 30 000 needles on the needle board and 6 000 needles per linear meter. The needle-punching is conducted at a punching rate of 300 punches per square cm so that the resulting punching density is 18 000 punches per square cm. This process pushes fibres from the fibre batts 12.2 and 12.3 through the screen 12.1, thereby bonding the fibre batts 12.2 and 12.3 to the screen 12.1 and to each other.

In different embodiments, the needle-punching process is conducted once or several times, on either side depending on the thickness required. The average thickness of the completed fibre batt is not more than about 3 mm. The Applicant has found that, if the material is much thicker than 3 mm, absorption by the wound dressing is slower and the ability of the wound dressing to "hold and lift" exudate from a wound becomes less effective. Particularly, where a number of layers of the wound dressing of the invention are placed on, or in, a wound which is producing a large amount of fluid, and in which the lower layers become saturated, the Applicant has found that, if the wound dressing is thicker than about 3 mm, transfer of the fluid through successive layers of the wound dressing is less effective. Thus, in use, the wound dressing of the invention may be used in several layers. It may also be folded or rolled for insertion into a wound cavity.

A complete fibre batt with the middle screen as described above was tested by the South African Bureau of Standards (SABS). The test results are tabulated below:

TABLE 1

| Tests | Results - SABS samples No. R2455A & R2455 B | Requirements as stated in CKS 464:1993 (as amended) | Methods of test, CKS 464:1993 (as amended) subclause reference |
|---|---|---|---|
| Construction | The dressing consists of 3 layers and a woven inner layer sandwiched between the 2 outer layers. The dressing has been needle-punched to create adhesion between the 3 layers. | — | Visual Examination |
| Fibre composition, % Outer layers (non-woven fabric) | All polyester | Cotton, viscose or thermobonding fibres(e.g. polypropylene) | 6.5 |
| Inner layer (woven fabric) | Cotton and polyester | — | |
| Mass per unit area, g/m$^2$ | 745 | — | 6.6 Determined on the composite sample |
| Bursting strength, kPa | 3819 | — | 6.7 Determined on the composite sample |
| Sterility | Does not comply | Sterile - packed dressings shall be sterile | 6.15 |
| Fluorescence Non-woven Woven fabric | Occasional spots Fluorescent | Not more than occasional point of intense blue fluorescence | 6.9 |
| Absorption rate, s | 1.1 | 10 max | 6.10 |
| Ash content, g/kg | 0,3 | 5 max | 6.11 |
| pH value of aqueous extract | 7 | 7 ∅ 2 extraction | BS3266 cold water |
| Freedom from dyes | No yellow, blue or green tint | Percolate may show a yellow colour but not green or blue tint | 6.14 |
| Steam sterilization | Complies | Shall not show any appreciable deterioration in handle | 6.16 |

Being of a different construction, the construction, the mass per unit area and the bursting strength results of samples No. R2455A and R2455B were not compared with the requirements of the above specification.

In Table 1 test samples No. R2455A and R2455B refer to test samples for properties specified in The South African Department of Trade and Industry specification: CKS 464: 1993 (as amended) for non-woven surgical dressings published by the SABS.

The wound dressing of the invention is a dispersion, high-absorbent, low adherent, disposable wound dressing.

It is an advantage of the invention illustrated that the wound dressing can be used for a wide variety of wounds including high exudating wounds, deep cavity wounds, superficial wounds (with ointments), burn wounds (where the low adherence properties of the wound dressing of the invention are important), transudating wounds, abscesses, ulcers, diabetic foot wounds, external cancer wounds, non-healing wounds, sinus wounds, and the like in both humans and animals. It is a further advantage of the invention illustrated that the wound dressing can be used as a surgical drain. It is a unique feature of the invention that both body fluids and bacteria can be dispersed from, or carried away from, the inside of a wound or cavity by a number of the wound dressings of the invention to the dressings on the outside of the wound or cavity. This enables wounds to heal from the inside and not from the outside. There is no breakdown in the material of the wound dressing after it has made contact with bodily fluids.

Generally, non-adherent absorbent dressings are made of gauze and porous fibres, including natural fibres such as cotton and synthetic fibres such as rayon and combinations thereof. A problem associated with such absorbent dressings is that the porous fibres absorb moisture or fluid from the wound. This leads to a phenomenon known as "strike through". Such wound dressings also to a certain extent, depending upon the type of dressing, tend to adhere to an exudating or transudating wound. Removal of such dressings from the wound often results in reopening of the wound and damage to newly formed granulating tissue.

It is an advantage of the invention illustrated that the tightly woven screen, which forms a discreet layer within the non-woven batt, serves to cause the exudate absorbed by the non-woven fabric part of the dressing to be dispersed along the screen. This serves to prevent or inhibit "strike through" and results in transport of the fluid away from the site of the wound. The advantage of this is that both fluid and bacteria are carried away from the wound thereby encouraging healing of the wound. It is a further advantage of the invention illustrated that the liquid permeable layer does not produce lint, fluff or the like, which are often associated with prior art wound dressings of which the Applicant is aware, and essentially does not adhere to the wound. This reduces both the trauma associated with changing dressings particularly in the case of serious wounds and prevents or inhibits damage to the healing wound caused by the removal of the dressing.

It is a further advantage of the invention illustrated that the three layers comprising the wound dressing can be bonded together by a single needle-punching process. Prior art processes known to the Applicant generally involve more than one needle-punching process to bond different layers together.

Without being bound thereby, the Applicant believes that the needle-punching process by which the wound dressing of the invention is fabricated and which involves a punching density of about 18 000 per square cm results in the dispersion action inside the dressing which distinguishes it from prior art absorbent dressings. It is the unique dispersion action inside the dressing which enables the dressing to "hold and lift" exudate or body fluids. Because of the dispersion action of the wound dressing of the invention, even once a dressing is saturated, a successive layer of the wound dressing will cause the fluids to be drawn away from the site of the wound so that healing can take place because of the removal of the fluids and associated bacteria from the wound. The success of the wound dressing of the invention, as a result of the dispersion action of the dressing, appears to be brought about by the choice of fibres and the needle-punching procedure used to fabricate the dressing.

What is claimed is:

1. A wound dressing comprising:
   a first and second absorbent layer, each absorbent layer being of a non-woven fabric of fibres, and each being able to absorb liquid; and
   a screen comprising polyester and cotton fibres between, and bonded to, the two absorbent layers so that the two absorbent layers and the screen form essentially a single, layered fabric body, wherein the screen and the two absorbent layers have a needle punched density of 1700–1900 punches per square cm, to thereby bond the screen and the absorbent layers.

2. The wound dressing as claimed in claim 1, in which the needle punched density is 1800 punches per square cm.

3. The wound dressing as claimed in claim 1, in which at least one liquid permeable layer, which is substantially non-adherent to human or animal tissue overlays, is bonded to, at least one of the absorbent layers.

4. The wound dressing as claimed in claim 3 inclusive, in which the liquid permeable layer is of foraminous or perforated synthetic polymeric material.

5. The wound dressing as claimed in claim 4, in which the synthetic polymeric material is selected from "MYLAR" (trade name) and "TELFA" (trade name).

6. The wound dressing as claimed in claim 3, in which the bonding between the or each liquid permeable layer and the or each absorbent layer is achieved by heat treatment under pressure.

7. The wound dressing as claimed in claim 1, in which each absorbent layer is constructed of porous polyester fibres.

8. The wound dressing as claimed in claim 1, in which the screen comprises 80% polyester and 20% cotton fibres.

9. The wound dressing as claimed in claim 1, in which the screen has a thread density of about 120 to 150 threads per square inch.

10. The wound dressing as claimed in claim 1, in which the screen has a yarn count of about 32 to 40.

11. The wound dressing as claimed in claim 1, in which the screen has a weight per unit area of approximately 100 g/m$^2$.

12. The wound dressing as claimed in claim 1, in which the absorbent layers of non-woven fabric are in the form of two fibre batts fabricated on a needleloom, each being made of 100% polyester fibre.

13. The wound dressing as claimed in claim 12, in which the fibre batts have a fineness of about 1.5 denier.

14. The wound dressing as claimed in claim 13, in which the fibre batts have a weight per unit area of approximately 300 g/m$^2$.

15. The wound dressing as claimed in claim 12 inclusive, in which the fibre batts have a fibre length of 7–8 cm.

16. The wound dressing as claimed in claim 1, in which the single, layered fabric body has a mass of about 700–750 g/m$^2$.

17. The wound dressing as claimed in claim 1, in which the single, layered fabric body has a thickness of not more than 3 mm.

18. A method of removing exudate from a wound, the method including the step of applying to an exuding wound at least one wound dressing as claimed in claim 1 inclusive.

19. A method of making a wound dressing, the method including the steps of fabricating two needle-punched fibre bans of fibres on a needleloom;

fabricating a tightly woven screen of polyester and cotton fibres;

locating the screen between the needle-punched fibre batts to form a composite structure in which the screen forms an inner layer between the two fibre batts; and needle-punching the composite structure on a needleloom to produce a single, layered fabric body in a needle-punching process in which the punching density is about 1700–1900 punches per square cm.

20. A method as claimed in claim 19, which includes the further step of securing a liquid permeable layer, which is substantially non-adherent to human or animal tissue, to at least one side of the single layered fabric body.

21. A method as claimed in claim 20 inclusive, which the liquid permeable layer is of foraminous or perforated synthetic polymeric material.

22. A method as claimed in claim 20 inclusive, in which the synthetic polymeric material is selected from "MYLAR" (trade name) and "TELFA" (trade name).

23. A method as claimed in claim 20 inclusive, in which securing the liquid permeable layer to the at least one side of the layered fabric body is achieved by heat treatment under pressure.

24. A method as claimed in claim 19, in which the needle-punched fibre batts are of polyester.

25. A method as claimed in claim 19 inclusive, in which the screen is fabricated of 80% polyester and 20% cotton yarns.

26. A method as claimed in claim 19 inclusive, in which the screen is fabricated to have a thread density of about 120 to 150 threads per square inch.

27. A method as claimed in claim 19 inclusive, in which the screen is fabricated to have a yarn count of about 32 to 40.

28. A method as claimed in claim 19 inclusive, in which the screen is fabricated to have a weight per unit area of approximately 100 g/m$^2$.

29. A method as claimed in claim 19 inclusive, in which the composite structure is needle-punched to produce the single layered fabric body having a mass of 700–750 g/m$^2$.

30. A method as claimed in claim 29, in which the composite structure is needle-punched so that the single layered fabric body has a thickness of not more than 3 mm.

31. A method as claimed in claim 19 inclusive, in which the fibre balls have a fineness of about 15 denier.

32. A method as claimed in claim 19 inclusive, in which the fibre bans are fabricated to have a weight per unit area of approximately 300 g/m$^2$.

33. A method of removing exudate from a wound, the method including the step of applying to an exuding wound at least one wound dressing made by a method as claimed in claim 19 inclusive.

* * * * *